United States Patent
Plant et al.

[11] Patent Number: 5,856,324
[45] Date of Patent: Jan. 5, 1999

[54] USE OF DIOXOMORPHOLINES FOR COMBAT ENDOPARASITES, DIOXOMORPHOLINES AND PROCESS FOR THEIR PRODUCTION

[75] Inventors: Andrew Plant, Leverkusen; Jürgen Scherkenbeck, Wermelskirchen; Peter Jeschke, Leverkusen; Achim Harder, Köln; Norbert Mencke, Leverkusen, all of Germany

[73] Assignee: Bayer Aktiengesellschaft, Leverkusen, Germany

[21] Appl. No.: 836,560

[22] PCT Filed: Oct. 30, 1995

[86] PCT No.: PCT/EP95/04255

§ 371 Date: May 2, 1997

§ 102(e) Date: May 2, 1997

[87] PCT Pub. No.: WO96/15121

PCT Pub. Date: May 23, 1996

[30] Foreign Application Priority Data

Nov. 10, 1994 [DE] Germany .................. 44 40 193.0

[51] Int. Cl.⁶ ............... A61K 31/535; C07D 413/00; C07D 265/30
[52] U.S. Cl. ...................... 514/235.5; 514/237.5; 514/239.5; 544/111; 544/170
[58] Field of Search ............... 514/235.5, 237.5, 514/239.5; 544/111, 170

[56] References Cited

FOREIGN PATENT DOCUMENTS 626375  11/1994  European Pat. Off. .
626376  11/1994  European Pat. Off. .
9403441  2/1994  WIPO .

OTHER PUBLICATIONS

Makromol. Chem. Rapid Commun. 6, 9, Helder, et al. (1985).
Makromol. Chem. Rapid Commun. 6, 607, Yonezawa, et al. (1985).
Makomol. Chem. 191, 1813, In't. Veld, et al. (1990).
Hasumi et al., "Lateritin . . . ", Journal of Antibiotics, vol. 46, No. 12 (Dec. 1993), pp. 1782–1787.
Chemical Abstracts, vol. 78, No. 9, Mar. 5, 1973, Abstract No. 58777; Shemyakin M.M. et al., "Synthesis and antimicrobial activity of analogs of enniatin antibiotics", pp. 2320–2334.
Chemical Abstracts, vol. 66, No. 18, May 1, 1967, Abstract No. 80398 M.M. Shemyakin, et al. "Depsipeptides. Mass spectrometric study of cyclodepsipeptides, 2,5–dioxomorpholines.", pp. 1539–1543.
Tetrahedron Letters, Bd. 26, Nr. 43, 1985, pp. 5257–5260, H.–G. Lerchen, et al. "Stereoselektive Synthese von D–Alpha–Hydroxycarbonsäuren enthaltenden Depsipeptiden aus L–Aminosäuren."

*Primary Examiner*—Mukund J. Shah
*Assistant Examiner*—Tamthom T. Ngo
*Attorney, Agent, or Firm*—Sprung Kramer Schaefer & Briscoe

[57] ABSTRACT

The present invention relates to the use of dioxomorpholines of the formula (I)

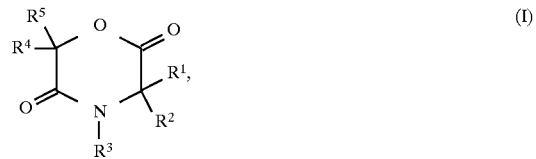

in which the radicals $R^1$ to $R^5$ have the meanings given in the description, their use for combating endoparasites and new dioxomorpholines and processes for their preparation.

10 Claims, No Drawings

USE OF DIOXOMORPHOLINES FOR COMBAT ENDOPARASITES, DIOXOMORPHOLINES AND PROCESS FOR THEIR PRODUCTION

This is a 371 application of PCT/EP 95/04255 filed on Sep. 30, 1995.

The present invention relates to the use of dioxomorpholines for combating endoparasites, to new dioxomorpholines and to processes for their preparation.

Certain dioxomorpholines and processes for their preparation are already known (compare, for example, Liebigs Ann. Chem. 1952 (1982), Makromol. Chem., Rapid Commun., 6 (1985), 607; Tetrachedron, 37 (1981), 2797; WO 9403441A1), but nothing has been disclosed to date pertaining to the use of these compounds against endoparasites.

The present invention relates to:
1. The use of dioxomorpholines of the formula (I)

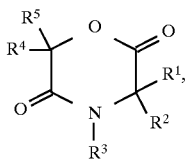

in which
R$^1$ and R$^2$ independently of one another represent hydrogen, straight-chain or branched alkyl, alkenyl, cycloalkyl, cycloalkylalkyl, aryl, arylalkyl, heteroaryl or heteroarylalkyl, which are optionally substituted, R$^1$ and R$^2$ together represent a spirocyclic radical which is optionally substituted, R$^3$ represent hydrogen, straight-chain or branched alkyl, cycloalkyl, aralkyl, aryl, heteroaryl or heteroarylalkyl, which are optionally substituted, R$^2$ and R$^3$ together with the atoms to which they are bonded represent a 5- or 6-membered ring, which can optionally be substituted, R$^4$ and R$^5$ independently of one another represent hydrogen, straight-chain or branched alkyl, alkenyl, cycloalkyl, cycloalkylalkyl aryl, arylalkyl, heteroaryl or heteroarylalkyl, which are optionally substituted, R$^4$ and R$^5$ represent a spirocyclic radical, which is optionally substituted, and optical isomers and racemates thereof, for combating endoparasites in medicine and veterinary medicine.

Dioxomorpholines of the formula (I)

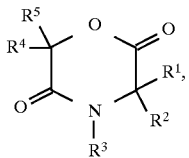

in which
R$^1$ and R$^2$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluoroenylmethoxycarbonyl(Fmoc)aminoalkyl, alkenyl, cycloalkyl or cycloalkylalkyl, or represent optionally substituted aryl, arylalkyl, heteroaryl or heteroarylalkyl, R$^1$ and R$^2$ together represent a spirocyclic radical, R$^3$ represent hydrogen, straight-chain or branched alkyl, cycloalkyl, aralkyl, aryl, heteroaryl or heteroarylalkyl, which are optionally substituted, R$^2$ and R$^3$ together with the atoms to which they are bonded represent a 5- or 6-membered ring, which can optionally be substituted, R$^4$ and R$^5$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl or cycloalkylalkyl, or represent optionally substituted aryl, arylalkyl, heteroaryl or heteroarylalkyl, R$^4$ and R$^5$ represent a spirocyclic radical, and optical isomers and racemates thereof, are preferably used for combating endoparasites in medicine and veterinary medicine.

The invention furthermore relates to:
2. new dioxomorpholines of the formula (I)

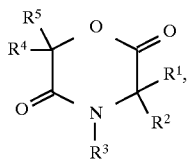

in which
R$^1$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl or cycloalkylalkyl, or represents optionally substituted aryl, arylalkyl, heteroaryl or heteroarylalkyl, R$^2$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl or cycloalkylalkyl, or represents optionally substituted aryl, arylalkyl, heteroaryl or heteroarylalkyl, $R^1$ and $R^2$ together can represent a spirocyclic radical, $R^3$ represents straight-chain or branched alkyl, cycloalkyl, aralkyl, aryl, heteroaryl or heteroarylalkyl, which are optionally substituted, $R^4$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloalkyl or cycloalkylalkyl, or represents optionally substituted aryl, arylalkyl, heteroaryl or heteroaryl alkyl, $R^5$ represents hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, alkoxycarbonyl alkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluor-enylmethoxycarbonyl(Fmoc)aminoalkyl, alkenyl, cycloalkyl or cycloalkylalkyl, or represents optionally substituted aryl, arylalkyl, heteroaryl or heteroarylalkyl, $R^4$ and $R^5$ together represent a spirocyclic radical with the proviso that in the case where $R^2$ represents the radicals hydrogen, methyl, benzyl or isopropyl and $R^3$ represents the radicals methyl or alkyl-substituted phenyl, $R^1$ represents radicals other than hydrogen, and optical isomers and racemates thereof.

3. Process for the preparation of the new dioxomorpholines of the formula (I) according to point 2 (above)

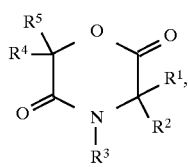

in which the radicals $R^1$ to $R^5$ have the meaning given under point 2, characterized in that a) open-chain depsipeptides of the formula (II)

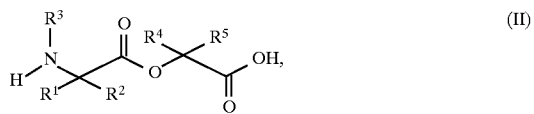

in which the radicals $R^1$ to $R^5$ have the abovementioned meaning, are cyclized in the presence of a diluent and in the presence of a coupling reagent, or b) compounds of the formula (I)

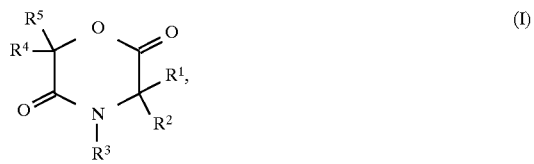

in which $R^3$ represents hydrogen and $R^1$, $R^2$, $R^4$ and $R^5$ have the abovementioned meaning, are reacted with compounds of the formula (III)

$$X—R^3 \qquad (III),$$

in which $R^3$ represents straight-chain or branched alkyl, cycloalkyl, aralkyl or heteroarylalkyl, which can optionally be substituted, X represents I, Cl or Br, in the presence of a diluent and a base.

4. Open-chain depsipeptides of the formula (II)

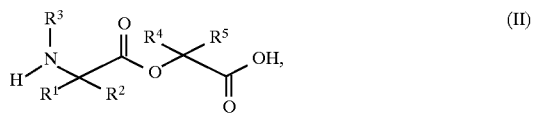

in which $R^1$ to $R^5$ have the meanings given under point 2.

5. Process for the preparation of the open-chain depsipeptides of the formula (II)

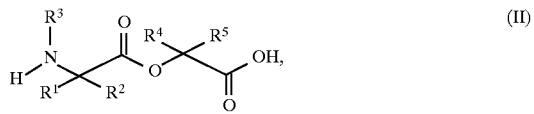

in which $R^1$ to $R^5$ have the meaning given above (under point 2), characterized in that a) compounds of the formula (IV)

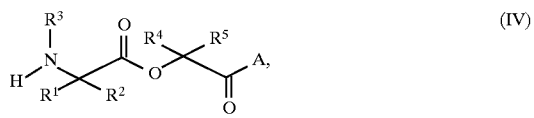

in which

A represents tert-butoxy, $R^1$ to $R^5$ have the abovementioned meanings, are hydrolysed in the presence of a diluent and a proton acid, or b) compounds of the formula (V)

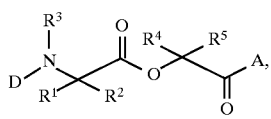

in which
 A represents tert-butoxy,
 D represents tert-butoxycarbonyl (—CO$_2^t$Bu),
 R$^1$ to R$^5$ have the abovementioned meanings,
 are hydrolysed in the presence of a diluent and a proton acid.

6. compounds of the formula (IV)

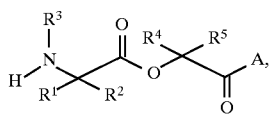

in which
 A represents tert-butoxy,
 R$^1$ to R$^5$ have the abovementioned meanings.

7. Process for the preparation of compounds of the formula (IV)

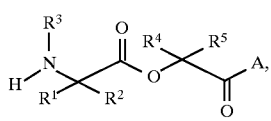

in which
 A represents tert-butoxy,
 R$^1$ to R$^5$ have the abovementioned meanings,
 characterized in that compounds of the formula (VI)

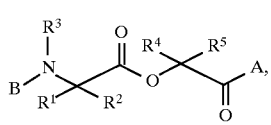

in which
 A for tert-butoxy,
 B for benzyl,
 R$^1$ to R$^5$ have the abovementioned meaning,
 are hydrogenolysed in the presence of a diluent and a catalyst.

8. Compounds of the formula (V)

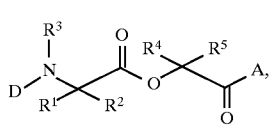

in which
 A represents tert-butoxy,
 D represents tert-butoxycarbonyl,
 R$^1$ to R$^5$ have the abovementioned meanings.

9. Process for the preparation of compounds of the formula (V)

in which
 A represents tert-butoxy,
 D represents tert-butoxycarbonyl,
 R$^1$ to R$^5$ have the abovementioned meanings.
 characterized in that compounds of the formula (VII)

in which
 D represents tert-butoxycarbonyl,
 R$^1$ to R$^3$ have the abovementioned meaning, in the form of their alkali metal salt, preferably their caesium salt, and an α-halogenocarboxylic acid of the formula (VIII)

in which
 X for Cl or Br and
 A represents tert-butoxy,
 R$^4$ and R$^5$ have the abovementioned meaning,
 are reacted in the presence of a diluent.

10. Compounds of the formula (VI)

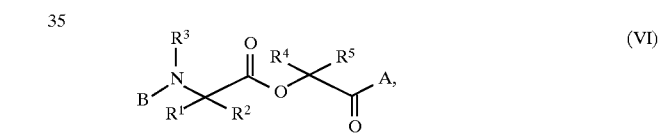

in which
 A for tert-butoxy,
 B represents benzyl,
 R$^1$ to R$^5$ have the abovementioned meaning.

11. Process for the preparation of compounds of the formula (VI)

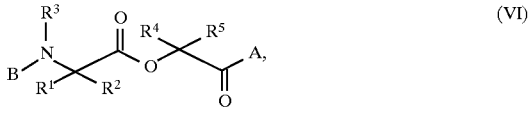

in which
 A represents tert-butoxy,
 B for benzyl and
 R$^1$ to R$^5$ have the abovementioned meaning,
 characterized in that compounds of the formula (IX)

in which
 B represents benzyl,
 R$^1$ to R$^3$ have the abovementioned meaning, in the form of their alkali metal salt, preferably their caesium salt, and an α-halogenocarboxylic acid of the formula (VIII)

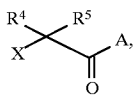

in which x represents Cl or Br,

A for tert-butoxy, $R^4$ and $R^5$ have the abovementioned meaning, are reacted in the presence of a diluent.

In the case where $R^5$ represents benzyl, the phenyl ring can be derivatized by customary substitution reactions.

The nitration described in the following may be mentioned as an example of such a substitution reaction.

In the following formulae, the substituents $R^1$ to $R^4$ have the meaning given (above) under point 1.

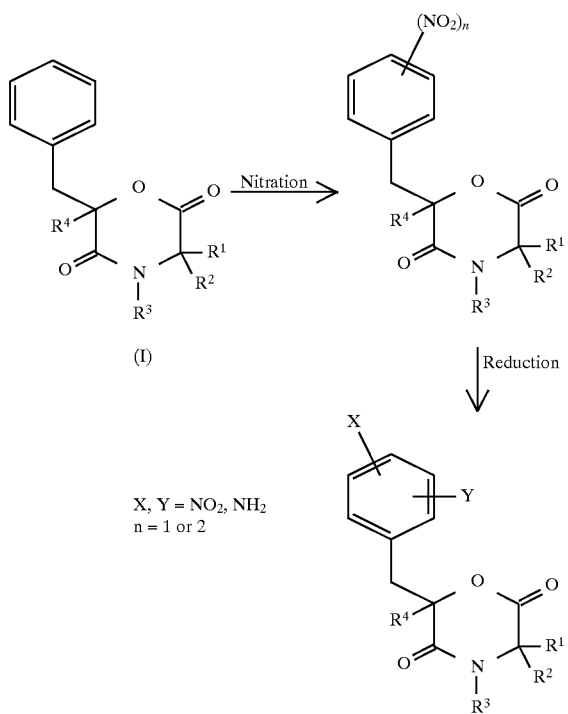

The nitro group (I) can be reduced to give mono- or bisamino-substituted phenyl derivatives. These can be acylated or alkylated in secondary reactions, for example

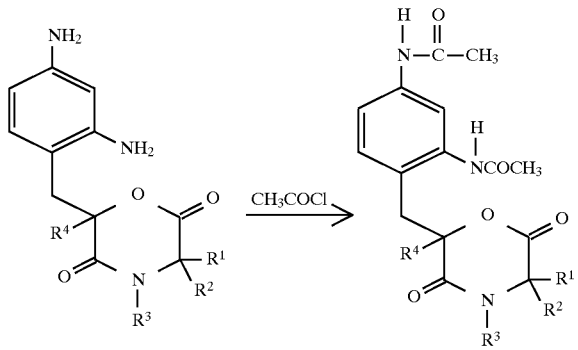

The dioxomorpholines of the formula (I) and acid addition salts and metal salt complexes thereof have a very good endoparasiticidal action, in particular anthelmintic action, and can preferably be employed in the field of veterinary medicine. The substances according to the invention surprisingly show a significantly better activity in combating worm diseases than structurally similar already-known compounds with the same activity.

Optionally substituted alkyl, by itself or as a constituent of a radical, in the general formulae denotes straight-chain or branched alkyl having preferably 1 to 9, in particular 1 to 5 carbon atoms. Optionally substituted methyl, ethyl, n- and i-propyl and n-, i- and t-butyl may be mentioned as examples and as preferred.

Optionally substituted alkenyl, by itself or as a constituent of a radical, in the general formulae denotes straight-chain or branched alkenyl having preferably 2 to 20, in particular 2 to 18 carbon atoms. Optionally substituted ethenyl, propen-1-yl, propen-2-yl and buten-3-yl may be mentioned as examples and as preferred.

Optionally substituted cycloalkyl in the general formulae denotes mono-, bi- and tricyclic cycloalkyl having preferably 3 to 10, in particular 3, 5 or 6 carbon atoms. Optionally substituted cyclopropyl, cyclobutyl, cyclopentyl, cyclohexyl, cycloheptyl, bicyclo[2.2.1]heptyl, bicyclo[2.2.2]octyl and adamantyl may be mentioned as examples and as preferred.

Optionally substituted alkoxy in the general formulae denotes straight-chain or branched alkoxy having preferably 1 to 6, in particular 1 to 4 carbon atoms. Optionally substituted methoxy, ethoxy, n- and i-propoxy and n-, o- and t-butoxy may be mentioned as examples and as preferred.

Optionally substituted alkylthio in the general formulae denotes straight-chain or branched alkylthio having preferably 1 to 6, in particular 1 to 4 carbon atoms. Optionally substituted methylthio, ethylthio, n- and i-propylthio and n-, o- and t-butylthio may be mentioned as examples and as preferred.

Halogenoalkyl in the general formulae contains 1 to 4, in particular 1 or 2 carbon atoms and preferably 1 to 9, in particular 1 to 5 identical or different halogen atoms, halogen atoms preferably being represented by fluorine, chlorine and bromine, in particular fluorine and chlorine. Trifluoromethyl, chloro-di-fluoromethyl, bromomethyl, 2,2,2-trifluoroethyl and pentafluoroethyl, perfluoro-t-butyl may be mentioned as examples.

Optionally substituted aryl in the general formulae preferably denotes optionally substituted phenyl or naphthyl, in particular phenyl.

Optionally substituted arylalkyl in the general formulae denotes arylalkyl which is optionally substituted in the aryl part and/or alkyl part and has preferably 6 or 10, in particular 8 carbon atoms in the aryl part (preferably phenyl or naphthyl, in particular phenyl) and preferably 1 to 4, in particular 1 or 2 carbon atoms in the alkyl part, it being possible for the alkyl part to be straight-chain or branched. Optionally substituted benzyl and phenylethyl may be mentioned as examples and as preferred.

Optionally substituted heteroaryl, by itself or as a constituent of a radical, in the general formulae denotes 5- to 7-membered rings having preferably 1 to 3, in particular 1 or 2 identical or different heteroatoms. Heteroatoms are represented by oxygen, sulphur or nitrogen. Optionally substituted furyl, thienyl, pyrazolyl, imidazolyl, 1,2,3- and 1,2,4-triazolyl, oxazolyl, isoxazolyl, thiazolyl, isothiazolyl, 1,2,3-, 1,3,4-, 1,2,4- and 1,2,5-oxadiazolyl, azepinyl, pyrrolyl, isopyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl may be mentioned as examples and as preferred.

The optionally substituted radicals of the general formulae can carry one or more, preferably 1 to 3, in particular 1 or 2 identical or different substituents. Substituents which may be listed as examples and as preferred are:

alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butyltio; halogenoalkyl having preferably 1 to 4, in particular 1 or 2 carbon atoms and preferably 1 to 5, in particular 1 to 3 halogen atoms, the halogen atoms being identical or different and the halogen atoms being preferably fluorine, chlorine or bromine, in particular fluorine, such as difluoromethyl and trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2 carbon atoms per alkyl group, such as methylamino, methylethyl-amino, n- and i-propylamino and methyl-n-butylamino; acylated amino such as $C_{1-4}$-alkylcarbonylamino, benzoylamino which can be substituted in the acyl part by halogen, nitro, trifluormethyl, trifluormethoxy, trifluoromethylthio; acyl radicals, such as carboxyl; carbalkoxy having preferably 2 to 4, in particular 2 or 3 carbon atoms, such as carbomethoxy and carboethoxy; alkylsulphinyl having 1 to 4, in particular 1 to 2 carbon atoms, halogenoalkylsulphinyl having 1 to 4, in particular 1 to 2 carbon atoms and 1 to 5 halogen atoms, such as trifluoromethylsulphinyl; sulphonyl (—$SO_3H$); alkylsulphonyl having preferably 1 to 4, in particular 1 or 2 carbon atoms, such as methylsulphonyl and ethylsulphonyl; halogenoalkylsulphonyl having 1 to 4, in particular 1 to 2 carbon atoms and 1 to 5 halogen atoms, such as trifluoromethylsulphonyl, perfluoro-t,n,s-butylsulphonyl; arylsulphonyl having preferably 6 or 10 arylcarbon atoms, such as phenylsulphonyl; acyl, aryl, aryloxy, heteroaryl or heteroaryloxy, which can in turn carry one of the above-mentioned substituents, and the forminino radical

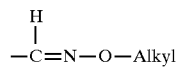

Preferred compounds of the formula (I) are those in which $R^3$ for straight-chain or branched $C_1$–$C_8$-alkyl, in particular methyl, ethyl, propyl, isopropyl, butyl, isobutyl, sec-butyl, tert-butyl, pentyl, isopentyl, secpentyl, hexyl, isohexyl, sec-hexyl, heptyl, isoheptyl, sec-heptyl, tert-heptyl, octyl, isooctyl, sec-octyl, 1-5-halogeno-$C_{1-4}$-alkyl, in particular trichloromethyl, trifluoromethyl, pentafluoroethyl chlorofluoroethyl, or hydroxy-$C_1$–$C_6$-alkyl, in particular hydroxymethyl or 1-hydroxyethyl, $C_1$–$C_4$-alkanoyloxy-$C_1$–$C_6$-alkyl, in particular acetoxymethyl or 1-acetoxyethyl, $C_1$–$C_4$-alkoxy-$C_1$–$C_6$-alkyl, in particular methoxymethyl or 1-methoxyethyl, aryl-$C_1$–$C_4$-alkyloxy-$C_1$–$C_6$-alkyl, in particular benzyloxymethyl or 1-benzyloxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl or carboxyethyl, $C_1$–$C_4$-alkoxycarbonyl-$C_1$–$C_6$-alkyl, in particular methoxycarbonylmethyl or ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl or carbamoylethyl, amino-$C_1$–$C_6$-alkyl, in particular aminopropyl or aminobutyl, $C_1$–$C_4$-alkylamino-$C_1$–$C_6$-alkyl, in particular methylaminopropyl or methylaminobutyl, $C_1$–$C_4$-dialkylamino $C_1$–$C_6$-alkyl, in particular dimethylaminopropyl or dimethylaminobutyl, guanido-$C_1$–$C_6$-alkyl, in particular guanidopropyl, $C_1$–$C_4$-alkoxycarbonylamino-$C_1$–$C_6$-alkyl, in particular tert-butoxycarbonylaminopropyl or tertbutoxycarbonylaminobutyl, 9-fluorenylmethoxycarbonyl(Fmoc)amino-$C_1$–$C_6$-alkyl, in particular 9-fluorenyl-methoxycarbonyl(Fmoc)aminopropyl or 9-fluorenylmethoxycarbonyl-(Fmoc)aminobutyl, $C_3$–$C_7$-cycloalkyl, in particular cyclopentyl, cyclohexyl or cycloheptyl, $C_3$–$C_7$-cycloalkyl-$C_1$–$C_4$-alkyl, in particular cyclopentylmethyl, cyclohexylmethyl or cycloheptylmethyl, phenyl or phenyl-$C_1$–$C_4$-alkyl, in particular phenylmethyl, which can optionally be substituted by radicals from the series consisting of halogen, in particular fluorine, chlorine bromine or iodine, hydroxyl, nitro, CN, $NH_2$, $C_1$–$C_4$-alkoxy, in particular methoxy or ethoxy or $C_1$–$C_4$-alkyl, in particular methyl, $R^1$, $R^2$, $R^4$ and $R^5$ independently of one another for hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, 1-5-halogeno-$C_{1-4}$-alkyl, in particular trichloromethyl, trifluoromethyl, pentafluoroethyl or chlorofluoroethyl, hydroxy-$C_1$–$C_6$-alkyl, in particular hydroxymethyl or 1-hydroxyethyl, $C_1$–$C_4$-alkanoyloxy-$C_1$–$C_6$-alkyl, in particular acetoxymethyl or 1-acetoxyethyl, $C_1$–$C_4$-alkoxy-$C_1$–$C_6$-alkyl, in particular methoxymethyl or 1-methoxyethyl, aryl-$C_1$–$C_4$-alkyloxy-$C_1$–$C_6$-alkyl, in particular benzyloxymethyl or 1-benzyloxy-ethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkyl sulphonyl-$C_1$–$C_6$-alkyl, in particular methylsulphonylethyl, $C_1$–$C_4$-alkoxycarbonyl-$C_1$–$C_6$-alkyl, in particular methoxycarbonylmethyl or ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl or carbamoylethyl, amino-$C_1$–$C_6$-alkyl, in particular aminopropyl or aminobutyl, $C_1$–$C_4$-alkylamino-$C_1$–$C_6$-alkyl, in particular methylaminopropyl or methylaminobutyl, $C_1$–$C_4$-dialkylamino-$C_1$–$C_6$-alkyl, in particular dimethylaminopropyl or dimethylaminobutyl, $C_2$–$C_8$-alkenyl, in particular vinyl, allyl or butenyl, $C_3$–$C_7$-cycloalkyl, in particular cyclopentyl, cyclohexyl or cycloheptyl, $C_3$–$C_7$-cycloalkyl-$C_1$–$C_4$-alkyl, in particular cyclopentylmethyl, cyclohexylmethyl or cycloheptylmethyl, phenyl, phenyl-$C_1$–$C_4$-alkyl, in particular phenylmethyl, thienylmethyl, thiazolylmethyl or pyridylmethyl, which can optionally be substituted by radicals from the series consisting of halogen, in particular fluorine, chlorine, bromine or iodine, hydroxyl, sulphonyl ($SO_3H$), CN, $NO_2$, amino, di($C_1$–$C_4$-alkyl)amino for example dimethylamino, acylated amino, for example acetylamino, benzoylamino, which can be further substituted in the acyl part by one of the above mentioned substituents, $C_1$–$C_4$-alkoxy, in particular methoxy or ethoxy, or $C_1$–$C_4$-alkyl, in particular methyl, and optical isomers and racemates thereof.

Particularly preferred compounds of the formula (I) are those in which $R^3$ for straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, secoctyl, 1-5-halogeno-$C_{1-4}$-alkyl, in particular trichloromethyl, trifluoromethyl, pentafluoroethyl or chlorofluoroethyl, hydroxy-$C_1$–$C_6$-alkyl, in particular hydroxymethyl or 1-hydroxyethyl, $C_1$–$C_4$-alkanoyloxy-$C_1$–$C_6$-alkyl, in particular acetoxymethyl or 1-acetoxyethyl, $C_1$–$C_4$-alkoxy-$C_1$–$C_6$-alkyl, in particular methoxymethyl or 1-methoxyethyl, aryl-$C_1$–$C_4$-alkyloxy-$C_1$–$C_6$-alkyl, in particular benzyloxymethyl or 1-benzyloxyethyl, $C_1$–$C_4$-alkoxycarbonylamino-$C_1$–$C_6$-alkyl, in particular tert-butoxycarbonylaminopropyl or tert-butoxycarbonylaminobutyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, or phenyl-$C_1$–$C_4$-alkyl, in particular phenylmethyl, which can optionally be substituted by one or more identical or different radicals from those mentioned above, $R^1$, $R^2$, $R^4$ and $R^5$ independently of one another for hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, 1-5-halogeno-$C_{1-4}$-alkyl, in particular trichloromethyl, trifluoromethyl, pentafluoroethyl or chlorofluoroethyl, hydroxy-$C_1$–$C_6$-alkyl, in particular hydroxymethyl, aryl-$C_1$–$C_4$-alkyloxy-$C_1$–$C_6$-alkyl, in particular benzyloxymethyl or 1-benzyloxyethyl, $C_1$–$C_4$-alkoxycarbonyl-$C_1$–$C_6$-alkyl, in particular methoxycarbonylmethyl or ethoxycarbonylethyl, $C_1$–$C_4$-arylalkoxycarbonyl-$C_1$–$C_6$-alkyl, in particular benzyloxycarbonylmethyl, $C_1$–$C_4$-alkylamino-$C_1$–$C_6$-alkyl, in particular methylaminopropyl or methylaminobutyl, $C_1$–$C_4$-dialkylamino-$C_1$–$C_6$-alkyl, in particular dimethylaminopropyl or dimethylaminobutyl, $C_2$–$C_8$-alkenyl, in particular vinyl, allyl or butenyt, $C_3$–$C_7$-cycloalkyl, in particular cyclopentyl, cyclohexyl or cycloheptyl, $C_3$–$C_7$-cycloalkyl-$C_1$–$C_4$-alkyl, in particular cyclopentylmethyl, cyclohexylmethyl or cycloheptylmethyl, phenyl, phenyl-$C_1$–$C_4$-alkyl, in particular phenylmethyl or thienylmethyl, which can optionally be substituted by one or more identical or different radicals from those mentioned above, and optical isomers and racemates thereof.

Especially preferred compounds of the formula (I) are those in which $R^3$ represent straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl or sec-octyl, $C_3$–$C_7$-cycloalkyl-$C_1$–$C_4$-alkyl, in particular cyclohexylmethyl, or phenyl-$C_1$–$C_4$-alkyl, in particular phenylmethyl, $R^1$, $R^2$, $R^4$ and $R^5$ independently of one another for hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl or sec-octyl, 1–5 halogeno-$C_{1-4}$-alkyl, in particular trichloromethyl, trifluoromethyl, pentafluoroethyl or chlorofluoroethyl, $C_2$–$C_8$-alkenyl, in particular vinyl or allyl, $C_3$–$C_7$-cycloalkyl-$C_1$–$C_4$-alkyl, in particular cyclohexylmethyl, phenyl-$C_1$–$C_4$-alkyl, in particular phenylmethyl or thienylmethyl, which can optionally be substituted by one or more identical or different radicals from those mentioned above, and optical isomers and racemates thereof.

The compounds of the general formula (I) can exist and be used in optically active, stereoisomeric forms or in the form of racemic mixtures. Preferably, the optically active stereoisomeric forms of the compounds of the general formula (I) are used.

The following compounds of the general formula (I) in which the radicals $R^1$ to $R^5$ have the following meaning, may be mentioned specifically:

| $R^1$ | $R^2$ | $R^3$ | $R^4$ | $R^5$ |
|---|---|---|---|---|
| $^i$Bu | H | Me | H | $^i$Bu |
| Me | Me | Me | H | $^i$Bu |
| $^i$Bu | H | Me | H | CF$_3$ |
| Me | Me | Me | H | Me |
| $^n$Pr | H | Me | H | Me |
| $^n$Pr | H | Bn | H | Me |
| $^n$Pr | H | Me | H | Bn |
| $^n$Pr | H | Bn | H | Bn |
| $^s$Bu | H | Me | H | Me |
| $^s$Bu | H | Bn | H | Me |
| $^s$Bu | H | Bn | H | Bn |
| $^i$Bu | H | Me | H | Ph |
| $^i$Bu | H | Bn | R | Ph |
| $^i$Bu | H | Bn | H | H |
| $^n$Pr | H | Me | H | H |
| $^n$Pr | H | Bn | H | H |
| $^i$Bu | H | Me | H | $^n$Pr |
| $^i$Bu | H | Me | H | —CH$_2$—⬡ |
| $^i$Bu | H | Me | H | —CH$_2$—[thienyl] |
| $^n$Pr | H | Me | H | —CH$_2$—[thienyl] |
| Me | Me | Me | H | H |
| $^i$Bu | H | Me | Me | Me |
| Me | Me | Me | Me | Me |
| —CH$_2$—⬡ | H | Me | H | Me |
| —CH$_2$—⬡ | H | Me | H | —CH$_2$—⬡ |
| H | $^i$Bu | Me | H | H |

| R¹ | R² | R³ | R⁴ | R⁵ |
|---|---|---|---|---|
| H | ⁱBu | Me | H | Bn |
| H | ⁱBu | Me | H | Me |
| H | ⁱBu | Bn | H | Me |

In this table and in the following table, in each case

Bu represents butyl

Me represents methyl

Bn represents benzyl

Pr represents propyl

Ph represents phenyl

Of the new compounds of the general formula (I), those in which the substituents have the abovementioned preferred definitions are preferred and particularly preferred.

The compounds of the general formula (I) are known in some cases (see above), or they can be obtained by the processes described above.

The new compounds of the formula (I) can be prepared by the process used by U. Schmidt et al. for macrocyclic peptide alkaloids (compare, for example: U. Schmidt et al. in Synthesis (1991) pages 294–300 [didemnin A, B and C]; Angew. Chem. 96 (1984) pages 723–724 [dolastatin 3]; Angew. Chem. 102 (1990) pages 562–563 [fenestin A]; Angew. Chem. 97 (1985) pages 606–607 [ulicyclamide]; J. Org. Chem. 47 (1982) pages 3261–3264).

The new compounds of the general formula (I) can be prepared by the processes described above under point 3.

If N-methyl-L-leucyl-D-lactic acid is employed as compounds of the formula (II) in process 3 for the preparation of the new dioxomorpholines (I), the process can be represented by the following equation:

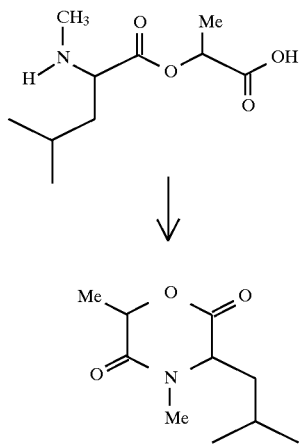

Formula (II) provides a general definition of the open-chain didepsipeptides required as starting substances for carrying out process 3a. In this formula, R¹ to R⁵ preferably represent those radicals which have already been mentioned as preferred for these substituents in connection with the description of the substances of the formula (I) according to the invention.

The didepsipeptides of the formula (II) used as starting materials are new. Their preparation is described later on below.

The following compounds of the general formula (II) in which the radicals R¹ to R⁵ have the following meaning may be mentioned specifically:

| R¹ | R² | R³ | R⁴ | R⁵ |
|---|---|---|---|---|
| ⁱBu | H | Me | H | ⁱBu |
| Me | Me | Me | H | ⁱBu |
| ⁱBu | H | Me | H | CF₃ |
| Me | Me | Me | H | Me |
| ⁿPr | H | Me | H | Me |
| ⁿPr | H | Bn | H | Me |
| ⁿPr | H | Me | H | Bn |
| ⁿPr | H | Bn | H | Bn |
| ˢBu | H | Me | H | Me |
| ˢBu | H | Bn | H | Me |
| ˢBu | H | Bn | H | Bn |
| ⁱBu | H | Me | H | Ph |
| ⁱBu | H | Bn | H | Ph |
| ⁱBu | H | Bn | H | H |
| ⁿPr | H | Me | H | H |
| ⁿPr | H | Bn | H | H |
| ⁱBu | H | Me | H | ⁿPr |
| ⁱBu | H | Me | H | —CH₂—cyclohexyl |
| ⁱBu | H | Me | H | —CH₂—thienyl |
| ⁿPr | H | Me | H | —CH₂—thienyl |
| Me | Me | Me | H | H |
| ⁱBu | H | Me | Me | Me |
| Me | Me | Me | Me | Me |
| —CH₂—cyclohexyl | H | Me | H | Me |
| —CH₂—cyclohexyl | H | Me | H | —CH₂—cyclohexyl |
| H | ⁱBu | Me | H | H |
| H | ⁱBu | Me | H | Bn |
| H | ⁱBu | Me | H | Me |
| H | ⁱBu | Bn | H | Me |

In process 3a, tetradepsipeptides are cyclized in the presence of diluents and suitable coupling reagents.

Suitable coupling reagents are all compounds which are suitable for linking an amine bond (compare, for example: Houben-Weyl, Methoden der Organischen Chemie [Methods of organic chemistry], Volume 15/2; Bodenzky et al., Peptide Synthesis 2nd ed., Wiley and Sons, New York 1976).

The following methods are preferably possible: active ester method with pentafluorophenol (PfP), N-hydroxysuccinimide or 1-hydroxybenzotriazole, coupling with carbodiimides, such as dicyclohexylcarbodiimide or N'-(3-dimethylaminopropyl)-N-ethylcarbodiimide (EDC), and the mixed anhydride method or coupling with phosphonium reagents, such as benzotriazol-1-yl-oxy-tris(dimethylaminophosphonium)-hexafluorophosphate (BOP), or bis-(2-oxo-3-oxazolidinyl)-phosphonium acid chloride (BOP-Cl), or with phosphonic acid ester reagents, such as cyanophosphonium acid diethyl ester (DEPC) and diphenylphosphoryl azide (DPPA).

Coupling with bis(2-oxo-3-oxazolidinyl)-phosphonium acid chloride (BOP-Cl) and N'-(3-dimethylaminopropyl)-N- ethylcarbodiimide (EDC) in the presence of 1-hydroxybenzotriazole (HOBt) is particularly preferred.

The reaction is carried out at temperatures from 0° to 150° C., preferably at 20° to 100° C., particularly preferably at room temperature.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl and dibutyl ether, glycol dimethyl ether and diglycol dimethyl ether, tetrahydrofuran and dioxane, and further ketones, such as acetone and methyl ethyl, methyl isopropyl and methyl isobutyl ketone, and also esters, such as methyl and ethyl acetate, and furthermore nitriles, such as, for example, acetonitrile and propionitrile, benzonitrile and glutarodinitrile, and moreover amides, such as, for example, dimethylformamide, dimethylacetamide and N-methylpyrrolidone, as well as dimethyl sulphoxide, tetramethylenesulphone and hexamethylphosphoric triamide.

The cyclization is carried out in the presence of a base.

Possible bases are inorganic and organic bases. Bases which may be mentioned are: alkali metal and alkaline earth metal hydroxides, carbonates, bicarbonates and alcoholates, and furthermore amines, such as, in particular, tertiary amines, for example trimethylamine, triethylamine, N-methylmorpholine, pyridine, picolines, N-ethylpyrrolidine, diazabicyclo-(4,3,0)-undecene (DBU), 1,4-diazabicyclo-(2,2,2)octane (DABCO), diazabicyclo(3,2,0)nonene (DBN) and ethyl-diisopropylamine.

The compounds of the formulae (II) and the bases are are employed in a ratio of 1:1 to 1:2 to one another. An approximately equimolar ratio is preferred.

After the reaction has been carried out, the diluent is distilled off and the compounds of the formula (I) are purified in the customary manner, for example by chromatography.

The didepsipeptides of the formula (II) used as starting compounds can be prepared by processes which are known per se, for example as described by H.-G. Lerchen and H. Kunz (Tetrahedron Lett. 26 (43) (1985) pages 5257–5260; 28 (17) (1987) pages 1873–1876) utilizing the esterification method according to B. F. Gisin (Helv. Chim. Acta 56 (1973) page 1476).

The aminoacids and 2-halogeno-carboxylic acid derivatives used as starting materials are known in some cases (compare, for example: N-methyl-amino acids: R. Bowmann et al. J. Chem. Soc. (1950) page 1346; J. R. McDermott et al. Can. J. Chem. 51 (1973) page 1915; H. Wurziger et al., Kontakte (Merck.Darmstadt) 3 (1987) page 8; 2-halogenocarboxylic acid derivatives: S. M. Birnbaum et al. J. Amer. Chem. Soc. 76 (1954) page 6054, C. S. Rondestvedt, Jr. et al. Org. Reactions 11 (1960) page 189 [Review]) or can be obtained by the processes described therein.

The open-chain didepsipeptides of the formula (II) can be obtained by a process which comprises the following, successive stages:

a) synthesis of the didepsipeptides of the formulae (V) and (VI) by processes 9 and 11:

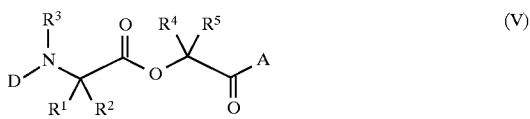

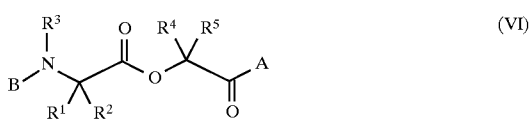

wherein B represents an N-terminal protective group, such as, for example, the benzyl or benzyloxycarbonyl group, or D represents tert-butyloxycarbonyl and A represents a C-terminal protective group, such as, for example, the tert-butoxy group.

For formula (VI), for example, this corresponds to the following equation:

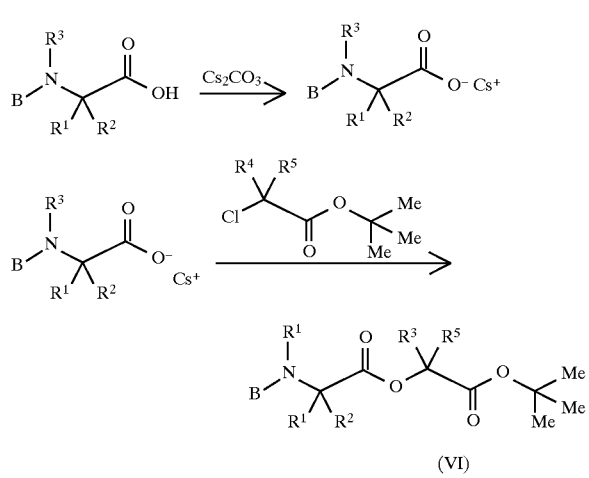

The preparation of the enantiomerically pure compounds of the formulae (V) and (VI) according to the invention can optionally also be carried out via separation of the diastereomers by customary methods, such as, for example, crystallization, by column chromatography or by Craig partition. The optimum process must be decided upon from case to case, and sometimes it is also expedient to use combinations of the individual processes.

At the end of this stage, removal of the N-terminal protective group from the compounds of the formula (VI) can be carried out in a manner known per se, for example by catalytic hydrogenation, for preparation of the derivatives of the formula (IV). The C-terminal protective group can be removed from derivatives of the formula (IV) in a manner known per se for preparation of the compounds of the formula (II).

The compounds of the formula (II) can also be obtained by simultaneously removing the N- and C-terminal protective groups from the derivatives of the formula (V).

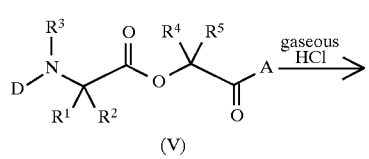

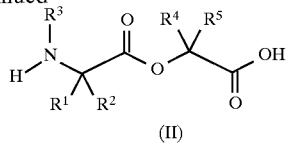

(II)

The removal of the N-terminal protective groups by hydrogenolysis in processes 7 is particularly preferably carried out with hydrogenating agents such as hydrogen in the presence of the customary hydrogenation catalysts, such as, for example, Raney nickel, palladium and platinum.

The process is preferably carried out using diluents. Possible diluents here are practically all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, methyl tert-butyl ether, glycol dimethyl ether and diglycol dimethyl ether, tetrahydrofuran and dioxane, esters, such as methyl and ethyl acetate, nitriles, such as, for example, acetonitrile and propionitrile, amides, such as, for example, dimethyl formamide, dimethylacetamide and N-methylpyrrolidone, as well as dimethylsulphoxide, tetramethylenesulphone and hexamethylphosphoric triamide; and furthermore also alcohols, such as methanol, ethanol, propanol, isopropanol, butanol, isobutanol, sec-butanol, tert-butanol, pentanol, isopentanol, sec-pentanol and tert-pentanol, and also water.

The reaction temperatures can be varied within a substantial range in the process according to the invention. The reaction is in general carried out at temperatures of between −20° C. and +200° C., preferably at temperatures between 0° C. and 120° C.

The process is in general carried out under normal pressure. However, it is also possible to carry out the process under increased pressure, in general between 10 and 100 bar.

The removal of the C-terminal protective groups by hydrolysis in processes 5a) and 5b) is preferably carried out using diluents.

Possible diluents here are practically all the inert organic solvents. These include, preferably, aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone and methyl ethyl, methyl isopropyl and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, and dimethyl sulphoxide, tetramethylenesulphone and hexamethylphosphoric triamide.

The reaction is carried out in the presence of inorganic or organic proton acids. Examples of these which may be mentioned are: hydrochloric acid, sulphuric acid, trifluoroacetic acid, acetic acid and formic acid.

The reaction is carried out at temperatures of between −20° and +50° C., preferably between −10° and +20° C., under normal or increased pressure. The reaction is preferably carried out under normal pressure.

The dioxomorpholines required as starting substances for carrying out the process 3b are already known (for example WO 940 3441 A1; Tetrahedron Letters 1983, 24, 1921; Liebigs An. Chem.; 1982, 1952; Biological and Biomechanical Performance of Biomaterials, 1986, 245, Editors P. Christel, A. Maunier, A. J. C. Lee).

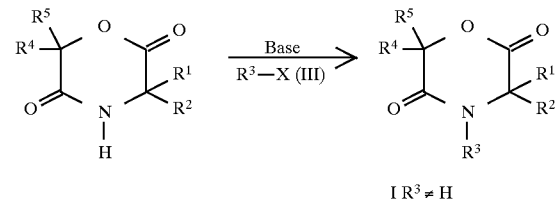

I R$^3$ ≠ H

The new compounds of the formula (I) can be prepared by the processes used for N-methylamino acids by N. L. Benoiton et al. (CAN. J. Chem., 1977, 55, 906; CAN. J. Chem., 1973, 51, 1915).

Possible alkylating reagents are alkyl halides, in particular alkyl iodides and alkyl bromides.

The reaction is carried out at temperatures from 0° to 150° C., preferably at 20° to 100° C., particularly preferably at room temperature.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachoride, chlorobenzene and o-dichlorobenzene, and furthermore ethers, such as diethyl ether and dibutyl ether, glycol dimethyl ether and diglycol dimethyl ether, tetrahydrofuran and dioxane, and furthermore ketones, such as acetone and methyl ethyl, methyl isopropyl and methyl isobutyl ketone, and in addition esters, such as methyl and ethyl acetate, and furthermore nitriles, such as, for example, acetonitrile and propionitrile, benzonitrile and glutarodinitrile, and moreover amides, such as, for example, dimethylformamide, dimethylacetamide and N-methylpyrrolidone, as well as dimethyl sulphoxide, tetramethylenesulphone and hexamethylphosphoric triamide.

The alkylation is carried out in the presence of a base.

Possible bases are inorganic and organic bases. Bases which may be mentioned are: alkali metal and alkaline earth metal hydroxides, carbonates, bicarbonates and alcoholates, and furthermore amines, such as, in particular, tertiary amines, for example trimethylamine, triethylamine, N-methylmorpholine, pyridine, picolines, N-ethylpyrrolidine, diazabicyclo-(4,3,0)-undecene (DBU), 1,4-diazabicyclo-(2,2,2)octane (DABCO), diazabicyclo(3,2,0)nonene (DBN), ethyl-diisopropylamine, NaH, organometallic bases, such as "butyllithium, lithium diisopropylamide (LDA) and lithium tetramethylpiperidide (LTMP).

The compounds of the formulae (II) and the bases are employed in a ratio of 1:1 to 5:1 to one another.

When the reaction has been carried out, the diluent is distilled off and the compounds of the formula (I) are purified in a customary manner, for example by chromatography.

The active compounds are suitable for combating pathogenic endoparasites which occur on humans and in animal keeping and animal breeding on stock, breeding, zoo, laboratory and test animals and hobby animals, and have a favourable toxicity to warm-blooded animals. They are active against all or individual stages of development of the pests and against resistant and normally sensitive species. By combating the pathogenic endoparasites, disease, fatalities and reductions in yield (for example production of meat, milk, wool, hides, eggs, honey and the like) should be diminished, so that more economical and easier animal keeping is possible by the use of the active compounds. The pathogenic endoparasites include cestodes, trematodes, nematodes and acanthocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.

From the order of the Enoplida, for example: Trichuris spp., Capillaria spp., Trichomosoides spp., Trichinelia spp.

From the order of the Rhabditia, for example: Micronema spp., Strongyloides spp.

From the order of the Strongylida, for example: Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp, Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The stock and breeding animals include mammals, such as, for example, cattle, horses, sheep, pigs, goats, camels, buffalo, donkeys, rabbits, fallow deer and reindeer, furbearing animals, such as, for example, mink, chinchillas and raccoons, birds, such as for example, chickens, geese, turkeys and ducks, fresh water and salt water fish, such as, for example, trout, carp and eels, reptiles and insects, such as, for example, honey bees and silkworms.

Laboratory and test animals include mice, rats, guinea pigs, golden hamsters, dogs and cats.

Pets include dogs and cats.

The compounds can be used both prophylactically and therapeutically.

The active compounds are used, directly or in the form of suitable formulations, enterally, parenterally, dermally, nasally, by treatment of the environment or with the aid of shaped articles containing the active compound, such as, for example, strips, sheets, tapes, collars, ear tags, limb bands and marking devices.

Enteral administration of the active compounds is made, for example, orally in the form of powders, tablets, capsules, pastes, granules, solutions, suspensions and emulsions for oral administration, boli, medicated feed or drinking water. Dermal administration is made, for example, in the form of dipping, spraying or pouring on and spotting on. Parenteral administration is made, for example, in the form of injection (intramuscular, subcutaneous, intravenous or intraperitoneal) or by implants.

Suitable formulations are:

Solutions, such as injection solutions, oral solutions, concentrates for oral administration after dilution, solutions for use on the skin or in body cavities, pour-formulations and gels;

Emulsions and suspensions for oral or dermal use and for injection; semi-solid formulations;

Formulations in which the active compound is processed in an ointment base or in an oil-in-water or water-in-oil emulsion base;

Solid formulations, such as powders, premixes or concentrates, granules, pellets, tablets, boli or capsules; aerosols and inhalation compositions, and shaped articles containing the active compound.

Injection solutions are administered intravenously, intramuscularly and subcutaneously.

Injection solutions are prepared by dissolving the active compound in a suitable solvent and adding any additives, such as solubilizing agents, acids, bases, buffer salts, antioxidants and preservatives. The solutions are subjected to sterile filtration and are transferred to containers.

Solvents which may be mentioned are: physiologically tolerated solvents, such as water, alcohols, such as ethanol, butanol, benzyl alcohol, glycerol, propylene glycol and polyethylene glycols, N-methyl-pyrrolidone, and mixtures thereof.

If appropriate, the active compounds can also be dissolved in physiologically tolerated vegetable or synthetic oils which are suitable for injection.

Solubilizing agents which may be mentioned are: solvents which promote dissolution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are used directly. Concentrates are used orally after prior dilution to the used concentration. Oral solutions and concentrates are prepared as described above for the injection solutions, but sterile working can be dispensed with.

Solutions for use on the skin are dripped on, brushed on, massaged in, sprayed on or misted on. These solutions are prepared as described above for the injection solutions.

It may be advantageous to add thickening agents during the preparation. Thickening agents are: inorganic thickening agents, such as bentonites, colloidal silicic acid and aluminium monostearate, organic thickening agents, such as cellulose derivatives, polyvinyl alcohols and copolymers thereof, acrylates and methacrylates.

Gels are applied to or brushed on the skin or introduced into body cavities. Gels are prepared by adding to solutions which have been prepared as described for the injection solutions thickening agents in an amount such that a clear composition having an ointment-like consistency is formed. Thickening agents which are employed are the thickening agents mentioned earlier on above.

Pour-on formulations are poured or sprayed onto limited areas of the skin, the active compound penetrating through the skin and having a systemic reaction.

Pour-on formulations are prepared by dissolving, suspending or emulsifying the active compound in suitable solvents or solvent mixtures which are tolerated by the skin. If appropriate, other auxiliaries such as dyestuffs, absorption-promoting substances, antioxidants, light protection agents and tackifying agents are added.

Solvents which may be mentioned are: water, alkanols, glycols, polyethylene glycols, polypropylene glycols, glycerol, aromatic alcohols, such as benzyl alcohol, phenylethanol and phenoxyethanol, esters, such as ethyl acetate, butyl acetate and benzyl benzoate, ethers, such as alkylene glycol alkyl ethers, such as dipropylene glycol monomethyl ether and diethylene glycol monomethyl ether and diethylene glycol mono-butyl ether, ketones, such as acetone and methyl ethyl ketone, aromatic and/or aliphatic hydrocarbons, vegetable or synthetic oils, DMF, dimethylacetamide, N-methylpyrrolidone and 2,2-dimethyl-4-oxy-methylene-1,3 -dioxolane.

Dyestuffs are all the dyestuffs approved for use on animals, and can be dissolved or suspended.

Absorption-promoting substances are, for example, DMSO, spreading oils, such as isopropyl myristate, dipropylene glycol pelargonate, silicone oils, fatty acid esters, triglycerides and fatty alcohols.

Antioxidants are sulphites or metabisulphites, such as potassium metabisulphite, ascorbic acid, butylated hydroxytoluene, butylated hydroxyanisole and tocopherol.

Light protection agents are, for example, novantisol acid.

Tackifying agents are, for example, cellulose derivatives, starch derivatives, polyacrylates, naturally occurring polymers, such as alginates, and gelatine.

Emulsions can be used orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and if appropriate further auxiliaries, such as dyestuffs, absorption-promoting substances, preservatives, antioxidants, light-protection agents and viscosity-increasing substances.

Hydrophobic phases (oils) which may be mentioned are: paraffin oils, silicone oils, naturally occurring vegetable oils, such as sesame oil, almond oil and castor oil, and synthetic triglycerides, such as caprylic/capric acid biglyceride, a triglyceride mixture with vegetable fatty acids of $C_{8-12}$ chain length or other specially selected naturally occurring fatty acids, partial glyceride mixtures of saturated or unsaturated fatty acids which may also contain hydroxyl groups, and mono- and diglycerides of the $C_8/C_{10}$ fatty acids.

Fatty acid esters, such as ethyl stearate, di-n-butyryl adipate, hexyl laurate, dipropylene glycol pelargonate, esters of a branched fatty acid of medium chain length with saturated fatty alcohols of $C_{16}$–$C_{18}$ chain length, isopropyl myristate, isopropyl palmitate, caprylic/capric acid esters of saturated fatty alcohols of $C_{12}$–$C_{18}$ chain length, isopropyl stearate, oleyl oleate, decyl oleate, ethyl oleate, ethyl lactate, wax-like fatty acid esters, such as synthetic duck uropygial gland fat, dibutyl phthalate, diisopropyl adipate, ester mixtures related to the latter and the like.

Fatty alcohols, such as isotridecyl alcohol, 2-octyldodecanol, cetylstearyl alcohol and oleyl alcohol.

Fatty acids, such as, for example, oleic acids, and their mixtures.

Hydrophilic phases which may be mentioned are: water, alcohols, such as, for example, propylene glycol, glycerol and sorbitol, and their mixtures.

Emulsifiers which may be mentioned are: nonionic surfactants, for example polyoxyethylated castor oil, polyoxyethylated sorbitan monooleate, sorbitan monostearate, glycerol monostearate, polyoxyethyl stearate and alkylphenol polyglycol ethers;

ampholytic surfactants, such as di-Na N-lauryl-β-iminodipropionate or lecithin;

anionic surfactants, such as Na- laury Isulphate, fatty alcohol ether-sulphates and mono/dialkyl polyglycol ether-orthophosphoric acid ester monoethynolamine salt.

Further auxiliaries which may be mentioned are: substances which increase the viscosity and which stabilize the emulsion, such as carboxymethylcellulose, ethylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be used orally, dermally or as an injection. They are prepared by suspending the active compound in a carrier liquid, if appropriate with the addition of further auxiliaries, such as wetting agents, dyestuffs, absorption-promoting substances, preservatives, antioxidants and light protection agents.

Carrier liquids which may be mentioned are all the homogeneous solvents and solvent mixtures.

Wetting agents (dispersing agents) which may be mentioned are the surfactants mentioned above.

Further auxiliaries which may be mentioned are those mentioned above.

Semi-solid formulations can be administered orally or dermally. They differ from the suspensions and emulsions described above only by their higher viscosity.

To prepare solid formulations, the active compound is mixed with suitable carrier substances, if appropriate with addition of auxiliaries, and the mixture is brought into the desired shape.

Carrier substances which may be mentioned are all the physiologically tolerated solid inert substances. Inorganic and organic substances are used as such. Inorganic substances are, for example, sodium chloride, carbonates, such as calcium carbonates, bicarbonates, aluminium oxides, silicic acids, aluminas, precipitated or colloidal silicon dioxide and phosphates.

Organic substances are, for example, sugars, cellulose, foodstuffs and feedstuffs, such as powdered milk, animal meals, cereal meals and shredded cereals and starches.

Auxiliaries are preservatives, antioxidants and dyestuffs, which have already been listed above.

Other suitable auxiliaries are lubricants and slip agents, such as, for example, magnesium stearate, stearic acid, talc and bentonites, disintegration-promoting substances, such as starch or crosslinked polyvinylpyrrolidone, binders, such as, for example, starch, gelatin or linear polyvinylpyrrolidone, and dry binders, such as microcrystalline cellulose.

The active compounds can also be present in the formulations as a mixture with synergists or with other active compounds which act against pathogenic endoparasites. Such active compounds are, for example, L-2,3,5,6-tetrahydro-6-phenylimidazothiazole, benzimidazolecarbamates, praziquantel, pyrantel and febantel.

Ready-to-use formulations contain the active compound in concentrations of 10 ppm –20 percent by weight, preferably of 0.1–10 percent by weight.

Formulations which are diluted before use contain the active compound in concentrations of 0.5–90% by weight, preferably 5–50% by weight.

In general, it has proved advantageous to administer amounts of about 1 to about 100 mg of active compound per kg of body weight per day to achieve effective results.

EXAMPLE A

In vivo nematode test

Haemonchus contortus/sheep

Sheep experimentally infected with Haemonchus contortus were treated after the end of the pre-patency period of the parasites. The active compounds were administered orally and/or intravenously as pure active compound.

The degree of effectiveness is determined by quantitatively counting the worm eggs excreted with the faeces, before and after treatment.

Complete cessation of the excretion of eggs after the treatment means that the worms have been expelled or are so severely damaged that they can no longer produce any eggs (effective dose).

The active compounds tested and the active dosages (effective dose) can be seen from the following table:

| Active compound Example No. | Effective dose in mg/kg |
| --- | --- |
| 2 | 10 |
| 4 | 10 |
| 5 | 10 |
| 6 | 10 |

Preparation Examples

1. Instructions for the preparation of compounds of the formula (I) according to the process 3a BOP-Cl (8.76 mmol) at a temperature of 0° C. was added to a solution of compound (II) (7.36 mmol) and Hünig base (25.6 mmol) in DMF (100 ml) and the mixture was subsequently stirred at room temperature for 24 hours. After this time, the same amounts of BOP-Cl and base were added and the mixture was stirred for a further 24 hours. The DMF was evaporated off by rotary evaporation in vacuo and methylene chloride was added to the residue. The solution was washed successively with 2N hydrochloric acid, saturated sodium bicarbonate solution and water, dried over magnesium sulphate and concentrated. The residue was purified by column chromatography with the eluent cyclohexane-ethyl acetate 5:1. Compounds of the formula (I) in which the substituents have the following meaning were obtained:

| Ex. No. | $R^1$ | $R^2$ | $R^{3*}$ | $R^4$ | $R^5$ | FAB-MS M/Z (%) |
| --- | --- | --- | --- | --- | --- | --- |
| 1 | H | $^i$Bu | Me | H | H | 186 (M + H, 100) |
| 2 | H | $^i$Bu | Me | H | Bn | 276 (M + H, 100) |
| 3 | H | $^i$Bu | Me | H | Me | 200 (M + H, 100) |
| 4 | H | —(CH$_2$)$_3$— | | H | Bn | 246 (M + H, 100) |
| 5 | H | —(CH$_2$)$_3$— | | H | Me | 170 (M + H, 100) |
| 6 | H | —(CH$_2$)$_4$— | | H | Bn | 260 (M + H, 100) |
| 7 | H | $^i$Bu | Bn | H | Me | 276 (M + H, 100) |
| 8 | H | $^i$Bu | H | H | Me | 186 (M + H, 100) |
| 9 | H | Bn | H | H | $^i$Bu | 262 (M + H, 100) |
| 10 | H | H | Me | H | $^i$Bu | 186 (M + H, 100) |
| 11 | H | $^i$Bu | H | H | Bn | 262 (M + H, 100) |
| 12 | H | $^n$Pr | Bn | H | Me | 262 (M + H, 74) |
| 13 | H | $^i$Bu | Me | H | —CH$_2$—⟨cyclohexyl⟩ | 282 (M + H, 100) |
| 14 | H | Bn | Me | H | Bn | 310 (M + H, 94) |
| 15 | H | $^i$Bu | Me | H | $^i$Pr | 228 (M + H, 100) |
| 16 | H | H | Me | H | Me | 144 (M + H, 100) |
| 17 | H | $^i$Bu | H | H | H | 172 (M + H, 100) |
| 18 | H | Bn | H | H | $^i$Pr | 248 (M + H, 100) |
| 19 | H | $^n$Pr | H | H | Me | 172 (M + H, 100) |
| 20 | H | —(CH$_2$)$_3$— | | H | Ph | 232 (M + H, 100) |
| 21 | H | H | H | H | —CH$_2$OBn | 236 (M + H, 100) |
| 22 | H | $^i$Bu | H | H | Ph | 248 (M + H, 100) |

*For $R^3$ = H, BOP (see p. 30) is the reagent of choice

2. General instructions for preparation of the compounds of the formula (I) according to process 3b NaH (30 mmol) was added in portions to a solution of the compounds (I) ($R^3$=H, 10 mmol) and (III) (80 mmol) in THF (30 ml) and the mixture was subsequently stirred at room temperature for 24 hours. The solution was acidified with 5% strength aqueous citric acid and extracted with methylene chloride (2×100 ml). The organic phase was dried over magnesium sulphate and concentrated in vacuo. The crude product was purified by column chromatography with the eluent cyclohexane-ethyl acetate. Compounds of the formula (I) in which the substituents have the following meaning were obtained:

| Ex. No. | $R^1$ | $R^2$ | $R^3$ | $R^4$ | $R^5$ | Physical Data FAB-MS M/Z (%) |
| --- | --- | --- | --- | --- | --- | --- |
| 3 | H | $^i$Bu | Me | H | Me | 200 (M + H, 100) |
| 7 | H | $^i$Bu | Bn | H | Me | 276 (M + H, 100) |
| 23 | H | $^i$Bu | Et | H | Me | |
| 24 | H | $^i$Bu | $^n$Pr | H | Me | |
| 25 | H | Me | Me | H | Me | |
| 26 | H | Me | Et | H | Me | |
| 27 | H | $^i$Bu | Bn | H | H | |
| 28 | H | $^i$Bu | Et | H | H | |
| 29 | H | Me | Me | H | H | |
| 30 | H | Me | Et | H | H | |

3. Instructions for preparation of the compounds of the formula (II) according to process 5a HCL gas was passed into a solution of the tert-butyl ester of the formula (IV) (1.61 mmol) in methylene chloride (40 ml) at 0°C. for 1.5 hours. The mixture was then warmed to room temperature and subsequently stirred for 12 hours. The solution was evaporated on a rotary evaporator and the residue was dried under a high vacuum. The residue was dissolved in water, the solution was added dropwise to a suspension of a basic ion exchanger (0.60 g) in 5 ml of water and the mixture was stirred for 3 hours, filtered and concentrated. After drying under a high vacuum, the product was reacted without further purification.

Compounds of the formula (II) in which the substituents have the following meaning were obtained according to these instructions:

| Ex. No. | $R^1$ | $R^2$ | $R^3$ | $R^4$ | $R^5$ |
|---------|-------|-------|-------|-------|-------|
| II-1    | H     | $^t$Bu | Me   | H     | H     |
| II-2    | H     | $^t$Bu | Me   | H     | Bn    |
| II-3    | H     | $^t$Bu | Me   | H     | Me    |
| II-4    | H     | $^t$Bu | Bn   | H     | Me    |
| II-5    | H     | H      | Me   | H     | $^t$Bu |

4. Instructions for the preparation of the compounds of the formula (II) according to process 5b HCl gas was passed into a solution of the tert-butyl ester of the formula (V) (1.61 mmol) in methylene chloride (40 ml) at 0° C. for 1.5 hours. The mixture was then warmed to room temperature and subsequently stirred for 12 hours. The solution was evaporated on a rotary evaporator and the residue was dried under a high vacuum. The residue was dissolved in water, the solution was added dropwise to a suspension of a basic ion exchanger (0.60 g) in 5 ml of water and the mixture was stirred for 3 hours, filtered and concentrated. After drying under a high vacuum, the product was reacted without further purification.

Compounds of the formula (II) in which the substituents have the following meaning were obtained according to these instructions:

| Ex. No. | $R^1$ | $R^2$    | $R^3$ | $R^4$ | $R^5$ |
|---------|-------|----------|-------|-------|-------|
| II-6    | H     | —(CH$_2$)$_3$— |  | H     | Bn    |
| II-7    | H     | —(CH$_2$)$_3$— |  | H     | Me    |
| II-8    | H     | —(CH$_2$)$_4$— |  | H     | Bn    |
| II-9    | H     | $^t$Bu   | H     | H     | $^t$Bu |
| II-10   | H     | Bn       | H     | H     | $^t$Bu |

5. Instructions for the preparation of the compounds of the formula (IV) according to process 7

A solution of a compound of the formula (VI) (9.50 mmol) in dioxane (50 ml) was hydrogenated in the presence of Pd(OH)$_2$/C (20% Pd; 600 mg) until the uptake of hydrogen had ended (about 2 hours). After the catalyst had been filtered off, compound (VII) was obtained in virtually quantitative yield and was further reacted without additional purification.

Compounds of the formula (IV) in which the substituents have the following meaning were obtained according to these instructions:

| Ex. No. | $R^1$ | $R^2$ | $R^3$ | $R^4$ | $R^5$ |
|---------|-------|-------|-------|-------|-------|
| IV-1    | H     | $^t$Bu | Me   | H     | H     |
| IV-2    | H     | $^t$Bu | Me   | H     | Bn    |
| IV-3    | H     | $^t$Bu | Me   | H     | Me    |
| IV-4    | H     | $^t$Bu | Bn   | H     | Me    |
| IV-5    | H     | H      | Me   | H     | $^t$Bu |

6. Process for the preparation of the compounds of the formula (V) according to process 9

The aminoacid of the formula (VII) (0.40 mol) was dissolved in 1400 ml of ethanol and 800 ml of water, a 20% strength caesium carbonate solution (390 ml) was added and the mixture was stirred at room temperature for 2 hours. It was then concentrated, the residue was dissolved in water (2000 ml) and the solution was freeze-dried. 0.40 mol of this caesium salt was initially introduced into 1000 ml of dimethylformamide, 0.40 mol of the chlorocarboxylic acid of the formula (VIII) was added at room temperature and the mixture was stirred at room temperature for 20 hours. The solution was concentrated, the residue was poured into water (1000 ml) and the mixture was extracted four times with ethyl acetate, dried over sodium sulphate and concentrated. The residue was reacted further without additional purification.

The compounds of the formula (V) in which the substituents have the following meaning were obtained analogously:

| Ex. No. | $R^1$ | $R^2$    | $R^3$ | $R^4$ | $R^5$ |
|---------|-------|----------|-------|-------|-------|
| V-1     | H     | —(CH$_2$)$_3$— |  | H     | Bn    |
| V-2     | H     | —(CH$_2$)$_3$— |  | H     | Me    |
| V-3     | H     | —(CH$_2$)$_4$— |  | H     | Bn    |
| V-4     | H     | $^t$Bu   | H     | H     | $^t$Bu |
| V-5     | H     | Bn       | H     | H     | $^t$Bu |

7. Instructions for the preparation of the compounds of the formula (VI) according to process 11

The aminoacid of the formula (IX) (0.40 mol) was dissolved in 1400 ml of ethanol and 800 ml of water, a 20% strength caesium carbonate solution (390 ml) was added and the mixture was stirred at room temperature for 2 hours. It was then concentrated, the residue was dissolved in water (2000 ml) and the solution was freeze-dried. 0.40 mol of this caesium salt was initially introduced into 1000 ml of dimethylformamide, 0.40 mol of the chlorocarboxylic acid of the formula (VIII) was added at room temperature and the mixture was stirred at room temperature for 20 hours. The solution was concentrated, the residue was poured into water (1000 ml) and the mixture was extracted four times with ethyl acetate, dried over sodium sulphate and concentrated. The residue was reacted further without additional purification.

The compounds of the formula (VI) in which the substituents have the following meaning were obtained analogously:

| Ex. No. | $R^1$ | $R^2$  | $R^3$ | $R^4$ | $R^5$ |
|---------|-------|--------|-------|-------|-------|
| VI-1    | H     | $^t$Bu | Me    | H     | H     |
| VI-2    | H     | $^t$Bu | Me    | H     | Bn    |
| VI-3    | H     | $^t$Bu | Me    | H     | Me    |
| VI-4    | H     | $^t$Bu | Bn    | H     | Me    |
| VI-5    | H     | H      | Me    | H     | $^t$Bu |

Example for carrying out the nitration

3-Isobutyl-4-methyl-6-(2,4-dinitrophenyl)-methyl-morpholine-2,5-dione

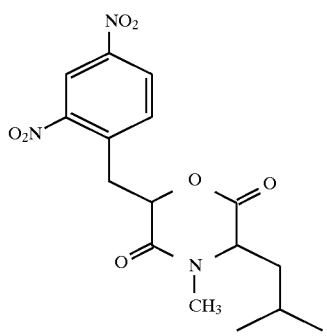

3-Isobutyl-4-methyl-6-benzyl-morpholine-2,5-dione (2.00 g, 7 mmol) was added to a solution of ice-cooled nitric acid (20 ml, 98% strength) and the mixture was subsequently stirred at 0° C. for 0.5 hours and then at room temperature for 1 hour. The solution was poured onto ice and then extracted with methylene chloride. The organic phase was dried over magnesium sulphate and concentrated in vacuo. The crude product was purified by column chromatography with the mobile phase cyclohexane-ethyl acetate (5:1). Yield=1.26 g, 56% of theory.

Compounds of the formula (I) in which the substituents have the following meaning were obtained

| Ex. No. | $R^1$ | $R^2$ | $R^3$ | $R^4$ | $R^5$ | FAB-MS M/Z (%) |
|---|---|---|---|---|---|---|
| 31 | H | $^i$Bu | Me | H | —CH$_2$—(phenyl with NO$_2$, NO$_2$) | 366 (M + H, 14) |
| 32 | H | —(CH$_2$)$_3$— | | H | —CH$_2$—(phenyl with O$_2$N, NO$_2$) | 366 (M + H, 14) |

Example of reduction of the nitro group on the phenyl ring

EXAMPLE 33
3-isobutyl-4-methyl-6-(2-amino-4-nitrophenyl)methyl-morpholine-2,5-dione and 3-isobutyl-4-methyl-6-(4-amino-2-nitrophenyl)methyl-morpholine-2,5-dione

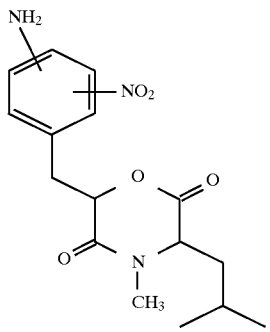

3-isobutyl-4-methyl-6-(2,4-dinitrophenyl)-methyl-morpholine-2,5-dione (0.50 g, 1.37 mmol) was hydrogenated in dioxane (40 ml) in the presence of Pd(OH)$_2$ (20 mol%) until the starting material could no longer be detected by means of thin-layer chromatography. The catalyst was filtered off and the solvent was concentrated in vacuo. The crude products were purified by column chromatography.

Total yield=0.20 g, 49% of theory, FAB-MS M/Z(%) 336 (M+H, 14)

EXAMPLE 34
3-Isobutyl -4-methyl-6-(2,4-diaminophenyl)methyl-morpholine-2,5-dione

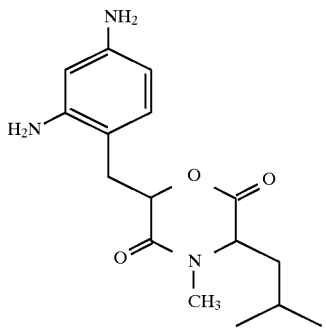

3-Isobutyl-4-methyl-6-(2,4-dinitrophenyl)methyl-morpholine-2,5-dione (1.20 g, 3.28 mmol) was hydrogenated in methanol (116 ml) and water (1.16 ml) in the presence of Raney-Nickel (33 g) until the uptake of hydrogen had ended. The catalyst was filtered off and the solvent was evaporated off on a rotary evaporator in vacuo.

Yield=0.84 g, 84% of theory, FAB-MS M/Z (%) 306 (M+H, 40)

EXAMPLE 35
3-Isobutyl-4-methyl -6-(2,4-diacetamidophenyl)m ethyl-morpholine-2,4-dione

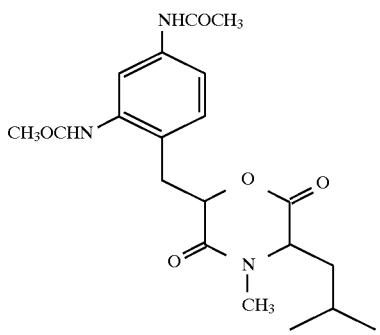

3-Isobutyl4-methyl-6-(2,4-diaminophenyl)methyl-morpholine-2,5 -dione(34) (0.50 g, 1.7 mmol) was dissolved in Dichloromethane (20 ml). Triethylamine (0.50 ml, 3.6 mmol) and acetylchloride (0.26 ml, 36 mmol) were added at 20° C. and the reaction mixture was then heated under reflux for 24 h. After coding, the solution was diluted with dichloromethane (50 ml) and then washed with dilute hydrochloric acid (2M, 10 ml), saturated sodium hydrogen carbonate solution (10 ml) and dried over sodium sulfate. The drying agent was removed by filtration and the solvent removed in vacuo. The residue was purified by flash chromatography on silica gel using the eluent ethyl acetate: cyclohexane (1:10) according 0.40 g (63% of theory) of product.

FAB-MS M/Z (%) 390 (M+H, 38).

EXAMPLE 36
3-Isobutyl-4-methyl -6-[2,4-bis-(4-chlorobenzamido) phenyl]methyl-morpholine-2,5-dione

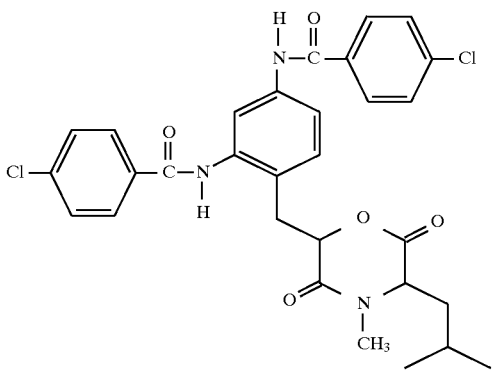

Compound 36 was prepared in a similar fashion to example 35 from 3-Isobutyl-4-methyl-6-(2,4-diaminophenyl)methyl-morpholine-2,5-dione (0.50 g) 4-chlorobenzoyl chloride (0.46 ml) and triethylamine (0.50 ml).

Yield=0.45 g, 45% of theory, FAB-MS M/Z (%) 582 (M+H, 10).

We claim:

1. A method of combating endoparasites comprising administering to a human or an animal an endoparasiticidally effective amount of at least one dioxomorpholine of the formula (I):

in which
$R^1$ and $R^2$ independently of one another represent hydrogen, straight-chain or branched alkyl, alkenyl, cycloalkyl, cycloalkylalkyl, aryl, aralkyl, heteroaryl or heteroarylalkyl which are optionally substituted, or $R^1$ and $R^2$ together represent a spirocycle radical which is optionally substituted, $R^3$ represents hydrogen, straight-chain or branched alkyl, cycloalkyl, aralkyl, aryl, heteroaryl or heteroarylalkyl, which are optionally substituted, or $R^2$ and $R^3$ together with the atoms to which they are bonded represent a 5- or 6-membered ring, which can optionally be substituted, $R^4$ and $R^5$ independently of one another represent hydrogen, straight-chain or branched alkyl, alkenyl, cycloalkyl, cycloalkylalkyl, aryl, arylalkyl, heteroaryl or heteroarylalkyl, which are optionally substituted, or $R^4$ and $R^5$ together represent a spirocyclic radical, which is optionally substituted, in the form of a racemic mixture or an optically active isomer thereof.

2. The method according to claim 1, wherein in the dioxomorpholine of formula (I):

$R^1$ and $R^2$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsuphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)-aminoalkyl, alkenyl, cycloalkyl or cycloalkylalkyl, or represent optionally substituted aryl, arylalkyl, heteroaryl or heteroarylalkyl, or $R^1$ and $R^2$ together represent a spirocyclic radical, $R^3$ represents hydrogen, straight-chain or branched alkyl, cycloalkyl, aralkyl, aryl, heteroaryl or heteroarylalkyl, which are optionally substituted, or $R^2$ and $R^3$ together with the atoms to which they are bonded represent a 5- or 6-membered ring, which can optionally be substituted, $R^4$ and $R^5$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)-aminoalkyl, alkenyl, cycloalkyl or cycloalkylalkyl, or represent optionally substituted aryl, arylalkyl, heteroaryl or heteroarylalkyl, or $R^4$ and $R^5$ together represent a spirocyclic radical, in the form of a racemic mixture or an optically active isomer thereof.

3. The method according to claim 1, wherein in the dioxomorpholine of formula (I):

$R^3$ represents straight-chain or branched $C_1$–$C_8$-alkyl, 1-5-halogeno-$C_{1-4}$-alkyl, hydroxy-$C_1$–$C_6$-alkyl, $C_1$–$C_4$-alkanoyloxy-$C_1$–$C_6$-alkyl, $C_1$–$C_4$-alkoxy-$C_1$–$C_6$-alkyl, aryl-$C_1$–$C_4$-alkyloxy-$C_1$–$C_6$-alkyl, mercapto-$C_1$–$C_6$-alkyl, $C_1$–$C_4$-alkylthio-$C_1$–$C_6$-alkyl, $C_1$–$C_4$-alkylsulphinyl-$C_1$–$C_6$-alkyl, $C_1$–$C_4$-alkylsulphonyl-$C_1$–$C_6$-alkyl, carboxy-$C_1$–$C_6$-alkyl, $C_1$–$C_4$-alkoxycarbonyl-$C_1$–$C_6$-alkyl, $C_1$–$C_4$-arylalkoxycarbonyl-$C_1$–$C_6$-alkyl, carbamoyl-$C_1$–$C_6$-alkyl, amino-$C_1$–$C_6$-alkyl, $C_1$–$C_4$-alkylamino-$C_1$–$C_6$-alkyl, $C_1$–$C_4$-dialkylamino, $C_1$–$C_6$-alkyl, guanido-$C_1$–$C_6$-alkyl, $C_1$–$C_4$-alkoxycarbonylamino-$C_1$–$C_6$-alkyl, 9-fluroenylmethoxycarbonyl(Fmoc)amino-$C_1$–$C_6$-alkyl, $C_3$–$C_7$-cycloalkyl, $C_3$–$C_7$-cycloalkyl-$C_1$–$C_4$-alkyl, phenyl or phenyl-$C_1$–$C_4$-alkyl, which can optionally be substituted by radicals selected from the group consisting of halogen, hydroxyl, nitro, CN, $NH_2$, $C_1$–$C_4$-alkoxy and $C_1$–$C_4$-alkyl, $R^1$, $R^2$, $R^4$ and $R^5$ independently of one another represent hydrogen, straight-chain or branched $C_1$–$C_8$-alkyl, 1-5-halogeno-$C_{1-4}$-alkyl, hydroxy-$C_1$–$C_6$-alkyl, $C_1$–$C_4$-alkanoyloxy-$C_1$–$C_6$-alkyl, $C_1$–$C_4$-alkoxy-$C_1$–$C_6$-alkyl, aryl-$C_1$–$C_4$-alkyloxy-$C_1$–$C_6$-alkyl, mercapto-$C_1$–$C_6$-alkyl, $C_1$–$C_4$-alkylthio-$C_1$–$C_6$-alkyl, $C_1$–$C_4$-alkylsulphinyl-$C_1$–$C_6$-alkyl, $C_1$–$C_4$-alkylsulphonyl-$C_1$–$C_6$-alkyl, $C_1$–$C_4$-alkoxycarbonyl-$C_1$–$C_6$-alkyl, $C_1$–$C_4$-arylalkoxycarbonyl-$C_1$–$C_6$-alkyl, carbamoyl-$C_1$–$C_6$-alkyl, amino-$C_1$–$C_6$-alkyl, $C_1$–$C_4$-alkylamino-$C_1$–$C_6$-alkyl, $C_1$–$C_4$-dialkylamino-$C_1$–$C_6$-alkyl, C$_2$–C$_8$-alkenyl, C$_3$–C$_7$-cycloalkyl, C$_3$–C$_7$-cycloalkyl-C$_1$–C$_4$-alkyl, phenyl, phenyl-C$_1$–C$_4$-alkyl, thienylmethyl, thiazolylmethyl or pyridylmethyl, which can optionally be substituted by radicals selected from the group consisting of halogen, hydroxyl, sulphonyl (SO$_3$H), CN, NO$_2$, amino, di(C$_1$–C$_4$-alkyl) amino, acylated amino, which can be further substituted in the acyl part by one of the above mentioned substituents, C$_1$–C$_4$-alkoxy and C$_1$–C$_4$-alkyl, in the form of a racemic mixture or an optically active isomer thereof.

4. The method according to claim 1, wherein in the dioxomorpholine of formula (I):

R$^3$ represents methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, trichloromethyl, trifluoromethyl, pentafluoroethyl, chlorofluoroethyl, hydroxymethyl, 1-hydroxyethyl, acetoxymethyl, 1-acetoxyethyl, methoxymethyl, 1-methoxyethyl, benzyloxymethol, 1-benzyloxyethyl, tert-butoxycarbonylaminopropyl, tert-butoxycarbonylaminobutyl, cyclopentyl, cyclohexyl, cycloheptyl, cyclopentylmethyl, cyclohexylmethyl, cycloheptylmethyl, or phenylmethyl which can optionally be substituted by one or more identical or different radicals selected from the group consisting of those mentioned above, R$^1$, R$^2$, R$^4$ and R$^5$ independently of one another for hydrogen, methyl, ethyl, propyl, isopropyl, butyl, isobutyl, sec-butyl, tert-butyl, sec-pentyl, hexyl, isohexyl, sec-hexyl, heptyl, isoheptyl, sec-heptyl, tert-heptyl, octyl, isooctyl, sec-octyl, trichloromethyl, trifluoromethyl, pentafluoroethyl, chlorofluoroethyl, hydroxymethyl, benzyloxymethyl, 1-benzyloxyethyl, methoxycarbonylmethyl, ethoxycarbonylethyl, benzyloxycarbonylmethyl, methylaminopropyl, methylaminobutyl, dimethylaminopropyl, dimethylaminobutyl, vinyl, allyl, butenyl, cyclopentyl, cyclohexyl, cycloheptyl, cyclopentylmethyl, cyclohexyl-methyl or cycloheptyl-methyl, phenyl, phenylmethyl or thienylmethyl, which can optionally be substituted by one or more identical or different radicals selected from the group consisting of those mentioned above, in the form of a racemic mixture or an optically active isomer thereof.

5. The method according to claim 1, wherein in the dioxomorpholine of formula (I):

R$^3$ represents methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl or sec-octyl, cyclohexylmethyl, or phenylmethyl, R$^1$, R$^2$, R$^4$ and R$^5$ independently of one another represent hydrogen, methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, trichloromethyl, trifluoromethyl, pentafluoroethyl, chlorofluoroethyl, vinyl, allyl, cyclohexylmethyl, phenylmethyl or thienylmethyl, which can optionally be substituted by one or more identical or different radicals selected from the group consisting of those mentioned above, in the form of a racemic mixture or an optically active isomer thereof.

6. An endoparasiticidal composition comprising a pharmaceutically acceptable carrier and an endoparasiticidally effective amount of at least one dioxomorpholine of the formula (I):

in which

R$^1$ and R$^2$ independently of one another represent hydrogen, straight-chain or branched alkyl, alkenyl, cycloalkyl, cycloalkylalkyl, aryl, aralkyl, heteroaryl or heteroarylalkyl which are optionally substituted, or R$^1$ and R$^2$ together represent a spirocycle radical which is optionally substituted, R$^3$ represents hydrogen, straight-chain or branched alkyl, cycloalkyl, aralkyl, aryl, heteroaryl or heteroarylalkyl, which are optionally substituted, or R$^2$ and R$^3$ together with the atoms to which they are bonded represent a 5- or 6-membered ring, which can optionally be substituted, R$^4$ and R$^5$ independently of one another represent hydrogen, straight-chain or branched alkyl, alkenyl, cycloalkyl, cycloalkylalkyl, aryl, arylalkyl, heteroaryl or heteroarylalkyl, which are optionally substituted, or R$^4$ and R$^5$ together represent a spirocyclic radical, which is optionally substituted, in the form of a racemic mixture or an optically active isomer thereof.

7. The composition according to claim 6, wherein in the dioxomorpholine of formula (I):

R$^1$ and R$^2$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsuphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)-aminoalkyl, alkenyl, cycloalkyl or cycloalkylalkyl, or represent optionally substituted aryl, arylalkyl, heteroaryl or heteroarylalkyl, or R$^1$ and R$^2$ together represent a spirocyclic radical, R$^3$ represents hydrogen, straight-chain or branched alkyl, cycloalkyl, aralkyl, aryl, heteroaryl or heteroarylalkyl, which are optionally substituted, or R$^2$ and R$^3$ together with the atoms to which they are bonded represent a 5- or 6-membered ring, which can optionally be substituted, R$^4$ and R$^5$ independently of one another represent hydrogen, straight-chain or branched alkyl having up to 8 carbon atoms, halogenoalkyl, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, alkoxycarbonylaminoalkyl, 9-fluorenylmethoxycarbonyl(Fmoc)-aminoalkyl, alkenyl, cycloalkyl or cycloalkylalkyl, or represent optionally substituted aryl, arylalkyl, heteroaryl or heteroarylalkyl, or $R^4$ and $R^5$ together represent a spirocyclic radical, in the form of a racemic mixture or an optically active isomer thereof.

8. The composition according to claim 6, wherein in the dioxomorpholine of formula (I):

$R^3$ represents straight-chain or branched $C_1$–$C_8$-alkyl, 1-5-halogeno-$C_{1-4}$-alkyl, hydroxy-$C_1$–$C_6$-alkyl, $C_1$–$C_4$-alkanoyloxy-$C_1$–$C_6$-alkyl, $C_1$–$C_4$-alkoxy-$C_1$–$C_6$-alkyl, aryl-$C_1$–$C_4$-alkyloxy-$C_1$–C6-alkyl, mercapto-$C_1$–$C_6$-alkyl, $C_1$–$C_4$-alkylthio-$C_1$–$C_6$-alkyl, $C_1$–$C_4$-alkylsulphinyl-$C_1$–$C_6$-alkyl, $C_1$–$C_4$-alkylsulphonyl-$C_1$–$C_6$-alkyl, carboxy-$C_1$–$C_6$-alkyl, $C_1$–$C_4$-alkoxycarbonyl-$C_1$–$C_6$-alkyl, $C_1$–$C_4$-arylalkoxycarbonyl-$C_1$–$C_6$-alkyl, carbamoyl-$C_1$–$C_6$-alkyl, amino-$C_1$–$C_6$- alkyl, $C_1$–$C_4$-alkylamino-$C_1$–$C_6$-alkyl, $C_1$–$C_4$-dialkylamino, $C_1$–$C_6$-alkyl, guanido-$C_1$–$C_6$-alkyl, $C_1$–$C_4$-alkoxycarbonylamino-$C_1$–$C_6$-alkyl, 9-fluroenylmethoxycarbonyl(Fmoc)amino-$C_1$–$C_6$-alkyl, $C_3$–$C_7$-cycloalkyl, $C_3$–$C_7$-cycloalkyl-$C_1$–$C_4$-alkyl, phenyl or phenyl-$C_1$–$C_4$-alkyl, which can optionally be substituted by radicals selected from the group consisting of halogen, hydroxyl, nitro, CN, $NH_2$, $C_1$–$C_4$-alkoxy and $C_1$–$C_4$-alkyl, $R^1$, $R^2$, $R^4$ and $R^5$ independently of one another represent hydrogen, straight-chain or branched $C_1$–$C_8$-alkyl, 1-5-halogeno-$C_{1-4}$-alkyl, hydroxy-$C_1$–$C_6$-alkyl, $C_1$–$C_4$-alkanoyloxy-$C_1$–$C_6$-alkyl, $C_1$–$C_4$-alkoxy-$C_1$–$C_6$-alkyl, aryl-$C_1$–$C_4$-alkyloxy-$C_1$–$C_6$-alkyl, mercapto-$C_1$–$C_6$-alkyl, $C_1$–$C_4$-alkylthio-$C_1$–$C_6$-alkyl, $C_1$–$C_4$-alkylsulphinyl-$C_1$–$C_6$-alkyl, $C_1$–$C_4$-alkylsulphonyl-$C_1$–$C_6$-alkyl, $C_1$–$C_4$-alkoxycarbonyl-$C_1$–$C_6$-alkyl, $C_1$–$C_4$-arylalkoxycarbonyl-$C_1$–$C_6$-alkyl, carbamoyl-$C_1$–$C_6$-alkyl, amino-$C_1$–$C_6$-alkyl, $C_1$–$C_4$-alkylamino-$C_1$–$C_6$-alkyl, $C_1$–$C_4$-dialkylamino-$C_1$–$C_6$-alkyl, $C_2$–$C_8$-alkenyl, $C_3$–$C_7$-cycloalkyl, $C_3$–$C_7$-cycloalkyl-$C_1$–$C_4$-alkyl, phenyl, phenyl-$C_1$–$C_4$-alkyl, thienylmethyl, thiazolylmethyl or pyridylmethyl, which can optionally be substituted by radicals selected from the group consisting of halogen, hydroxyl, sulphonyl ($SO_3H$), CN $NO_2$, amino, di($C_1$–$C_4$-alkyl) amino, acylated amino, which can be further substituted in the acyl part by one of the above mentioned substituents, $C_1$–$C_4$-alkoxy and $C_1$–$C_4$-alkyl, in the form of a racemic mixture or an optically active isomer thereof.

9. The composition according to claim 6, wherein in the dioxomorpholine of formula (I):

$R^3$ represents methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, trichloromethyl, trifluoromethyl, pentafluoroethyl, chlorofluoroethyl, hydroxymethyl, 1-hydroxyethyl, acetoxymethyl, 1-acetoxyethyl, methoxymethyl, 1-methoxyethyl, benzyloxymethol, 1-benzyloxyethyl, tert-butoxycarbonylaminopropyl, tert-butoxycarbonylaminobutyl, cyclopentyl, cyclohexyl, cycloheptyl, cyclopentylmethyl, cyclohexylmethyl, cycloheptylmethyl, or phenylmethyl which can optionally be substituted by one or more identical or different radicals selected from the group consisting of those mentioned above, $R^1$, $R^2$, $R^4$ and $R^5$ independently of one another for hydrogen, methyl, ethyl, propyl, isopropyl, butyl, isobutyl, sec-butyl, tert-butyl, sec-pentyl, hexyl, isohexyl, sec-hexyl, heptyl, isoheptyl, sec-heptyl, tert-heptyl, octyl, isooctyl, sec-octyl, trichloromethyl, trifluoromethyl, pentafluoroethyl, chlorofluoroethyl, hydroxymethyl, benzyloxymethyl, 1-benzyloxyethyl, methoxycarbonylmethyl, ethoxycarbonylethyl, benzyloxycarbonylmethyl, methylaminopropyl, methylaminobutyl, dimethylaminopropyl, dimethylaminobutyl, vinyl, allyl, butenyl, cyclopentyl, cyclohexyl, cycloheptyl, cyclopentylmethyl, cyclohexyl-methyl or cycloheptyl-methyl, phenyl, phenylmethyl or thienylmethyl, which can optionally be substituted by one or more identical or different radicals selected from the group consisting of those mentioned above, in the form of a racemic mixture or an optically active isomer thereof.

10. The composition according to claim 6, wherein in the dioxomorpholine of formula (I):

$R^3$ represents methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl or sec-octyl, cyclohexylmethyl, or phenylmethyl, $R^1$, $R^2$, $R^4$ and $R^5$ independently of one another represent hydrogen, methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, trichloromethyl, trifluoromethyl, pentafluoroethyl, chlorofluoroethyl, vinyl, allyl, cyclohexylmethyl, phenylmethyl or thienylmethyl, which can optionally be substituted by one or more identical or different radicals selected from the group consisting of those mentioned above, in the form of a racemic mixture or an optically active isomer thereof.

* * * * *